United States Patent [19]

Shumakov et al.

[11] 4,152,785
[45] May 8, 1979

[54] ARTIFICIAL HEART

[76] Inventors: Valery I. Shumakov, ulitsa Smolenskaya, 7, kv. 56; Moisei A. Lokshin, ulitsa 8 Marta, 7/5, kv. 12, both of Moscow, U.S.S.R.

[21] Appl. No.: 866,813

[22] Filed: Jan. 3, 1978

[51] Int. Cl.² ............................ A61F 1/24; A61M 1/03
[52] U.S. Cl. ........................................................ 3/1.7
[58] Field of Search .......... 3/1.7, 1; 128/1 D, DIG. 3

[56] References Cited

U.S. PATENT DOCUMENTS

| | | | |
|---|---|---|---|
| 3,733,616 | 5/1973 | Willis | 3/1.7 |
| 3,783,453 | 1/1974 | Bolie | 3/1.7 |
| 3,874,002 | 4/1975 | Kurpanek | 3/1.7 |
| 3,974,825 | 8/1976 | Normann | 3/1.7 X |
| 4,078,267 | 3/1978 | Cieszynski | 3/1.7 |

FOREIGN PATENT DOCUMENTS 438416  1/1975  U.S.S.R. ................................... 3/1.7

OTHER PUBLICATIONS

"Artificial Intracorporeal Heart" by F. W. Hastings et al., Transactions of the American Society for Artificial Internal Organs, vol. VII, 1961, pp. 323-325.
"Artificial Heart Ventricular Design Having Space and Performance Characteristics Comparable to the Heart" by Adair Rogers et al., Int. J. Engineering Science, vol. 10, No. 12, Dec. 1972, pp. 1037-1047.

*Primary Examiner*—Ronald L. Frinks
*Attorney, Agent, or Firm*—Steinberg & Blake

[57] ABSTRACT

An artificial heart comprising a rigid housing whose dimensions and shape are close to those of the natural heart. A rigid central partition divides the housing into two halves corresponding to the right and left hearts, respectively. Each half is divided by a rigid lateral partition into two chambers. One of these chambers is adjacent to the central partition; this is an auricle chamber. The second chamber is between said auricle chamber and the wall of the housing; this is a ventricle chamber. Each auricle chamber is divided by a flexible diaphragm into two cavities. One of these cavities adjoins the central partition and is intended to contain a working medium. The other cavity adjoins the lateral partition and is intended to receive blood. Each chamber of the ventricle is also divided by a flexible diaphragm into two cavities. One of these cavities adjoins the lateral partition and is intended to receive blood, whereas the second cavity adjoins the housing wall and is intended for the working medium. Installed in each of the lateral partitions are check valves which serve to communicate the blood cavities of the auricle chamber with those of the ventricle chamber and transfer blood from the auricle chamber to the ventricle chamber.

4 Claims, 2 Drawing Figures

ARTIFICIAL HEART

The present invention relates to cardiac surgery and, more specifically, to an artificial heart intended to replace completely the natural heart in clinical and experimental conditions.

There is known an artificial heart which is a four-chamber pump comprising two auricle chambers and two ventricle chambers. The two pairs of chambers, each including an auricle and a ventricle, serve as the right and left hearts, respectively. The right heart and left heart are both divided into an auricle and a ventricle by a partition. The partition has built-in check valves through which the ventricle and auricle communicate with each other during the diastole. The check valves are arranged in the central part of the partition and formed by the edges of through slots and leaf-type shut-off elements. Each of the auricles is a chamber receiving blood from the venous bed. The ventricles are interposed between the auricles and provided with working elements. Each of the working elements is a plate intended to act upon the blood during the systole and controlled by an electromechanical drive. Arranged at the outlets of the respective ventricles are the tricuspid valve of the pulmonary artery and the aortic valve.

During the diastole, blood is directed from the venous bed through the auricle and check valves to the ventricle. During the systole, the check valves close, and blood is forced from the ventricle into the aorta. The working element of the ventricle is controlled by the electromechanical drive.

The artificial heart under review is disadvantageous in that the auricle comprises a single blood cavity; this makes it difficult to measure the pressure and volume of the blood in the auricle, which is essential to control the artificial heart so as to improve the sensitivity to the venous return by introducing, for example, a correcting feedback. The fact that the slot-type check valves are arranged in the central part of the partition accounts for the formation of stagnation zones, which, in turn, affects the blood and can be the reason of thrombogenesis. In addition, the dimensions of the artificial heart under review are incommensurable with the anatomical parameters of the chest: the artificial heart is too long in the direction transverse to the chest.

There is further known an artificial heart, wherein the auricle is composed of two cavities. One of the cavities is intended to receive blood and is a tube with a single built-in inlet check valve. The second cavity is intended for a working medium and envelops the tube.

It is difficult to install this second artificial heart in the thoracic cavity because the shape of the former does not correspond to the anatomical dimensions of the latter.

The auricle, which comprises a tube and a cavity enveloping the tube, is too big. When installed in the thoracic cavity, it compresses the auricles and empty veins, which affects the hemodynamic characteristics and the venous return. In a number of cases, the implantation of an artificial heart of the type under review necessitates the removal of a part of the lung.

Like the artificial heart which was discussed first, this artificial heart does not make it possible to measure the instantaneous volume of blood in the auricle; as a result, it is impossible to measure the instantaneous venous return and provide conditions for accurate venous return control.

It is an object of the present invention to provide an artificial heart, wherein the dimensions of the auricle would correspond to the anatomical dimensions of the chest, which would rule out compression of the auricle.

It is another object of the invention to provide an artificial heart whose auricle design would facilitate the control and adjustment of the artificial heart's parameters and would make possible simple and accurate instantaneous venous return measurements without any contact with the blood.

It is a further object of the invention to provide for a better resistance to thrombogenic factors and improve the hemodynamic characteristics.

The foregoing objects are attained by providing an artificial heart comprising a rigid housing; a rigid solid central partition which divides the housing into two halves corresponding to the left heart and right heart, respectively; a lateral rigid partition in each of said halves, which divides the respective half into a ventricle chamber and an auricle chamber; a flexible diaphragm dividing each of the auricle chambers into two cavities one of which adjoins the central partition and is intended for the working medium, while the other adjoins said lateral partition and is intended for blood; a flexible diaphragm dividing each of the ventricle chambers into two cavities one of which adjoins the lateral partition and is intended to receive blood, whereas the other adjoins the wall of the housing and is intended for a working medium; check valves installed in each of the lateral partitions, which check valves serve to communicate the blood cavities of each auricle chamber and each ventricle chamber and force the blood from the auricle chamber to the ventricle chamber; an inlet pipe of the blood cavity of each of the auricle chambers, which inlet pipe is intended to communicate the respective auricle chamber with the venous bed of the patient; a check valve installed in each outlet pipe of the ventricle chamber; and a pipe of the working medium cavity of each of the ventricle chambers, which serves to communicate the respective ventricle chamber with a working medium source.

In the proposed artificial heart, the auricle chambers adjoin the central partition and are interposed between the ventricle chambers. As a result, the dimensions of the artificial heart correspond to those of the chest, and mechanical compression of the auricle is effectively prevented.

The auricle of the proposed artificial heart comprises two cavities divided by a diaphragm; this provides for simple and accurate instantaneous venous return measurements without any contact with the blood. Such measurements can be taken, for example, with the aid of a sensor of the end positions of the flexible auricle diaphragm.

According to the invention, blood pressure and volume measurements are to be carried out without any special sensitive elements. To make this possible, the artificial heart is provided with a current-carrying coating applied onto the surfaces of the central partition, facing the working medium cavities of the auricle. This current-carrying coating serves as a plate of a capacitance transducer. The other plate of said capacitance transducer is formed by the surface layer of the blood adjoining the diaphragm of the auricle.

This provides for simple and accurate measurements of the pressure and volume of blood in the auricle and a more effective venous return control, and also improves the sensitivity to the venous return, delivery value, etc.

According to the invention, the check valves installed in the lateral partitions are of the leaf type and arranged along the periphery of the partitions. This eliminates the formation of zones of stagnation and improves the resistance to thrombogenesis.

Other objects and advantages of the present invention will become more apparent from the following detailed description of a preferred embodiment thereof taken in conjunction with the accompanying drawings, wherein.

Figure 1:
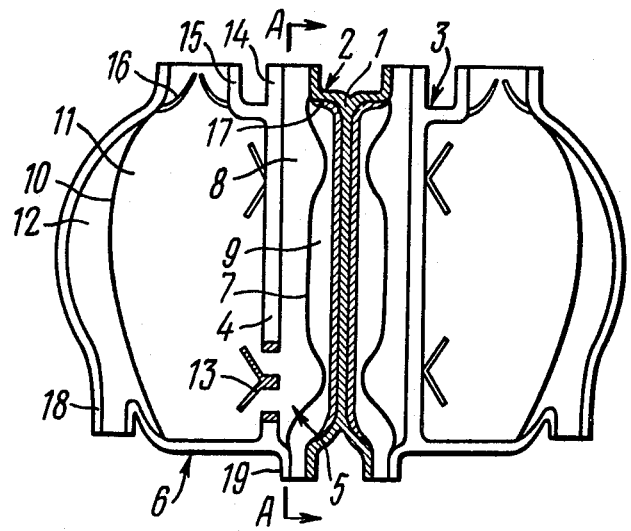
FIG. 1 is a diagram of an artificial heart in accordance with the invention.
Figure 2:
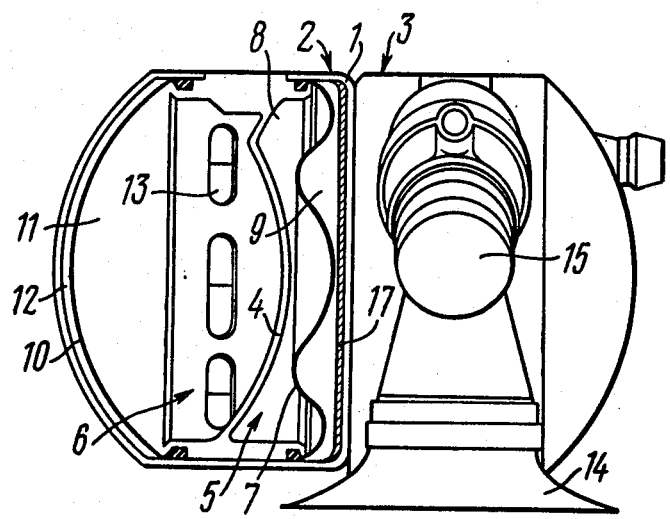
FIG. 2 is a view of an artificial heart in accordance with the invention, including a cross-section of one of its halves.

The diaphragm of FIG. 1 is intentionally simplified for a better understanding of operation of the proposed artificial heart, while FIG. 2 makes it clear that the shape and dimensions of the proposed artificial heart correspond to those of the natural heart.

Referring to the attached drawings, the artificial heart of this invention comprises a rigid housing whose shape and dimensions are close to those of the natural heart. The housing is divided by a rigid solid central partition 1 (FIGS. 1 and 2) into halves of an identical design, which are a left heart 2 and a right heart 3.

Each half is divided by a rigid lateral partition 4 into an auricle chamber 5 and a ventricle chamber 6. The auricle chamber 5 is divided by a flexible diaphragm 7 into a blood cavity 8 (FIG. 1) and a working medium cavity 9. The ventricle chamber 6 is divided by a flexible diaphragm 10 into a blood cavity 11 and a working medium cavity 12. Installed in each of the rigid lateral partitions 4 are check valves 13 (FIGS. 1 and 2) through which the blood cavities 8 of the auricle chambers 5 communicate with the blood cavities 11 of the ventricle chambers 6 during the diastole. The blood cavity 8 of each auricle chamber 5 communicates with the venous bed of the circulation through an inlet pipe 14 (FIG. 1).

The blood cavity 11 of each ventricle chamber 6 communicates with the arterial bed of the circulatory system through outlet pipes 15 provided with built-in outlet valves 16. The check valves 13 are formed by leaves overlapping slots arranged along the periphery of the rigid lateral partition 4.

Applied onto the internal surface of the central partition 1 is a current-carrying coating 17.

The working medium cavity 12 of each ventricle chamber 6 communicates with a working medium source through a pipe 18.

The working medium cavity 9 of each auricle chamber 5 communicates with the working medium source or with the atmosphere through a pipe 19.

The proposed artificial heart operates as follows.

It is installed in the thoracic cavity, in place of the natural heart.

From the venous beds of the systemic and pulmonary circulations, blood comes into the blood cavities 8 of the auricle chambers 5 through the inlet pipes 14. The volume of blood in the blood cavity 8 of the auricle chamber 5 and the position of the diaphragm 7 change according to the venous return value. The change in the position of the diaphragm 7 of the auricle chamber 5 brings about a change in the capacity of the transducer formed by the current-carrying coating 17 and the surface layer of the blood next to said diaphragm 7. As a result, at the output of said capacitance transducer there is produced a signal of a variable magnitude, which corresponds to the actual volume of blood in the auricle chamber 5, or the actual position of the diaphragm 7; this means that the magnitude of the signal corresponds, in fact, to the actual instantaneous venous return value.

Thus it is sufficient to apply the current-carrying coating 17 onto the surface of the central partition 1 on the side of the auricle chamber 5 to produce an actual venous return value signal without resorting to any sensors directly contacting the blood. This improves the effectiveness of control and makes it possible to bring the characteristics of the artificial heart in correspondence with the physiological parameters.

The use of the working medium cavity 9 makes it possible to improve the accuracy of the venous return control by directing the working medium to said cavity 9 through the pipe 19 as required by the operating conditions.

In addition, the proposed arrangement of the chambers 5 and 6 makes it possible to reduce the transverse size of the artificial heart so that the overall dimensions of the artificial heart correspond to those of the thorcic cavity.

During the diastole, the auricle chambers 5 communicate with the ventricle chambers 6 through the check valves 13 (FIGS. 1 and 2) located along the periphery of the rigid lateral partition 4. The peripheral arrangement of the check valves 13, through which blood leaves the auricle chambers 5 to enter the ventricle chambers 6, rules out the formation of zones of stagnation and improves the resistance to thrombogenesis.

During the systole, the check valves 13 close. The blood, which filled the ventricle chambers 6 during the diastole, is forced out through the outlet valve 16 (FIG. 1), built into the outlet pipe 15, whereupon the blood is directed back to the circulatory system. The ejection of the blood is controlled by the presence of the working medium (pressurized gas). The flexible diaphragm 10 moves under the action of the gas directed to the working medium cavity 12 through the pipe 18.

What is claimed is:

1. An artificial heart comprising: a rigid housing whose dimensions and shape are close to those of the natural heart; a rigid solid central partition dividing said housing into two halves corresponding to the left heart and right heart, respectively; a rigid lateral partition in each of said halves, which divides the respective half into two chambers one of which adjoins said central partition and is an auricle chamber, whereas the other is interposed between said auricle chamber and the wall of said housing and is a ventricle chamber; a flexible diaphragm arranged in each of said auricle chambers and dividing the respective auricle chamber into two cavities one of which adjoins said central partition and is intended for a working medium, whereas the other adjoins said lateral partition and is intended for blood; a flexible diaphragm arranged in each of said ventricle chambers and dividing the respective ventricle chamber into two cavities one of which adjoins said lateral partition and is intended for blood, whereas the other adjoins the wall of said housing and is intended for the working medium; check valves installed in each of said lateral partitions, which check valves serve to communicate said blood cavities of said auricle and ventricle chambers and transfer blood from the auricle chamber to the ventricle chamber; an inlet pipe of said blood cavity of each of said auricle chambers, intended to communicate the respective auricle chamber with the venous bed of the patient; an outlet pipe of said blood cavity of each of said ventricle chambers, intended to communicate the respective ventricle chamber with the arterial bed of the patient; a check valve in each of said outlet pipes of each of said ventricle chambers; a pipe of the working medium cavity of each of said auricle chambers, intended to communicate the respective auricle chamber with a working medium source.

2. An artificial heart as claimed in claim 1, provided with a current-carrying coating applied onto the surface of said central partition facing said working medium cavity of the auricle.

3. An artificial heart as claimed in claim 1, wherein said check valves in said lateral partitions are leaf-type valves arranged along the periphery of said lateral partitions.

4. An artificial heart as claimed in claim 2, wherein said check valves of said lateral partitions are leaf-type valve arranged along the periphery of said lateral partitions.

* * * * *